(12) United States Patent
Seikai Armenta

(10) Patent No.: US 11,298,527 B2
(45) Date of Patent: Apr. 12, 2022

(54) AUTONOMOUS NEUROSTIMULATION UNIT

(71) Applicant: Aitaro Seikai Armenta, Rincon de Soto (ES)

(72) Inventor: Aitaro Seikai Armenta, Rincon de Soto (ES)

( * ) Notice: Subject to any disclaimer, the term of this patent is extended or adjusted under 35 U.S.C. 154(b) by 0 days.

(21) Appl. No.: 16/766,565

(22) PCT Filed: Jul. 4, 2018

(86) PCT No.: PCT/ES2018/070479
§ 371 (c)(1),
(2) Date: May 22, 2020

(87) PCT Pub. No.: WO2019/141886
PCT Pub. Date: Jul. 25, 2019

(65) Prior Publication Data
US 2021/0001111 A1    Jan. 7, 2021

(30) Foreign Application Priority Data

Jan. 17, 2018 (ES) .................................. P201830051

(51) Int. Cl.
*A61N 1/04* (2006.01)
*A61N 1/10* (2006.01)
*A61H 39/00* (2006.01)

(52) U.S. Cl.
CPC ......... *A61N 1/0492* (2013.01); *A61N 1/0456* (2013.01)

(58) Field of Classification Search
CPC ...... A61N 1/0456; A61N 1/0492; A61N 1/10; A61N 1/36031; A61H 39/002
See application file for complete search history.

(56) References Cited

U.S. PATENT DOCUMENTS

| | | |
|---|---|---|
| 2005/0182455 A1 | 8/2005 | Thrope et al. |
| 2007/0276456 A1 | 11/2007 | Hwang |
| 2008/0249587 A1 | 10/2008 | Cho et al. |
| 2009/0112278 A1* | 4/2009 | Wingeier ............. A61B 5/4064 607/45 |
| 2014/0148872 A1* | 5/2014 | Goldwasser ....... A61N 1/36082 607/45 |

(Continued)

FOREIGN PATENT DOCUMENTS

| | | |
|---|---|---|
| ES | 2218246 T3 | 11/2004 |
| JP | H0759867 A | 3/1995 |
| WO | 2014165111 A2 | 10/2014 |

OTHER PUBLICATIONS

International Search Report for International Application No. PCT/ES2018/070479 (Dec. 17, 2018) (4 Pages).

*Primary Examiner* — Carl H Layno
*Assistant Examiner* — Anh-Khoa N Dinh
(74) *Attorney, Agent, or Firm* — Lucas & Mercanti, LLP

(57) ABSTRACT

An autonomous neurostimulation unit used in the modulation of the nervous system is provided and has: at least one pair of pads, each formed by at least one inner layer of ceramic; an intermediate layer; and a conductive alloy coating. The material of the layer of coating is different and has different conductivity in each of the pads of the pair. The unit can be used in the modulation of the nervous system, with neurostimulation methods that are adapted to each patient.

5 Claims, 2 Drawing Sheets

(56) References Cited

U.S. PATENT DOCUMENTS

| | | | |
|---|---|---|---|
| 2015/0273215 A1* | 10/2015 | Nabutovsky | A61N 1/36017 607/59 |
| 2015/0306386 A1 | 10/2015 | Alpert et al. | |
| 2016/0346530 A1* | 12/2016 | Jeffery | A61N 1/36031 |
| 2016/0346535 A1 | 12/2016 | Kim | |
| 2017/0252562 A1* | 9/2017 | Goldwasser | A61N 1/0456 |

* cited by examiner

AUTONOMOUS NEUROSTIMULATION UNIT

CROSS REFERENCE TO RELATED APPLICATION

This Application is a 371 of PCT/ES2018/070479 filed on Jul. 4, 2018, which claims the benefit of Spanish Patent Application No. P201830051, filed Jan. 17, 2018, which is incorporated herein by reference.

OBJECT OF THE INVENTION

The object of the invention refers to an autonomous neurostimulation unit used in the modulation of the nervous system.

BACKGROUND OF THE INVENTION

The information processing system of the organism is based on the transmission of sensory impulses produced by neural ion exchange. These neural impulses or electrophysiological excitations are transmitted through different channels or routes of the nervous system. These routes or channels are the different trajectories of the nerve branches that come from the spinal column and that connect from one point of the organism to another. That in correct operation of electrophysiological transmission have an optimal frequency, obtaining perfect emission of the neural impulses that allow the maximum efficiency of the channels of the nervous system.

The processing of information by the human organism of stimulus from the outside world through an INPUT of information is processed by our sensory organs, in this case the nervous system through the channels or routes of the peripheral nervous system. This information is processed by neural impulses that reflect a response to the outside world through an OUTPUT of information to the outside world.

In the current state of the art, methods or techniques for the purpose of restoring health and well-being in a person are already known; in the most modern area there exist inventions that use electric currents such as the PJ-A-5036068 at pressure points to restore health. The same points are used as in traditional medicine because they are specific points or resonators of the meridians or channels of communication with less impedance.

Technical Problem to be Resolved

Traditional oriental medicinal theory considers that the disease is an imbalance of the body's vital energy and that until this imbalance of energy is corrected the disease will persist, but what these methods work are those points of the peripheral nerve with less impedance by pressure or currents to correct the imbalance, but they do not correct the actual frequency of the nervous system and what is more, they are not portable; therefore, while one is connected to them and movements are restricted.

DESCRIPTION OF THE INVENTION

The object of the invention is an autonomous neurostimulation unit which helps to improve the correct operation of this process of electrophysiological transfer by artificial excitation systems outside the human body. To this end, a system is developed to modulate the electrical information of the nervous system without the application of external electrical stimulation; the unit is formed by at least a pair of pads; the pads use the energy of the nervous system itself as they are placed on the nerve channels or routes with less impedance.

The pads for modulation of electrical energy of the nervous system generate differentials of pulsating current at physiological level at the different points of the body, concentrating more or less potential of the human body's own energy. This helps to repair the imbalance and to recover the optimal frequency of the nervous system and does so without any type of external energy.

In addition, not carrying cable or batteries, they can be used, and lead a normal life without the least interference.

Other configurations and advantages of the invention can be deduced from the following description, and from the subsidiary claims.

DESCRIPTION OF THE DRAWINGS

To better understand the object of the invention, a preferential form of embodiment is represented in the attached figures, subject to accessory changes that do not essentially alter it. In this case.

DETAILED DESCRIPTION OF A PREFERENTIAL EMBODIMENT

Figure 1:
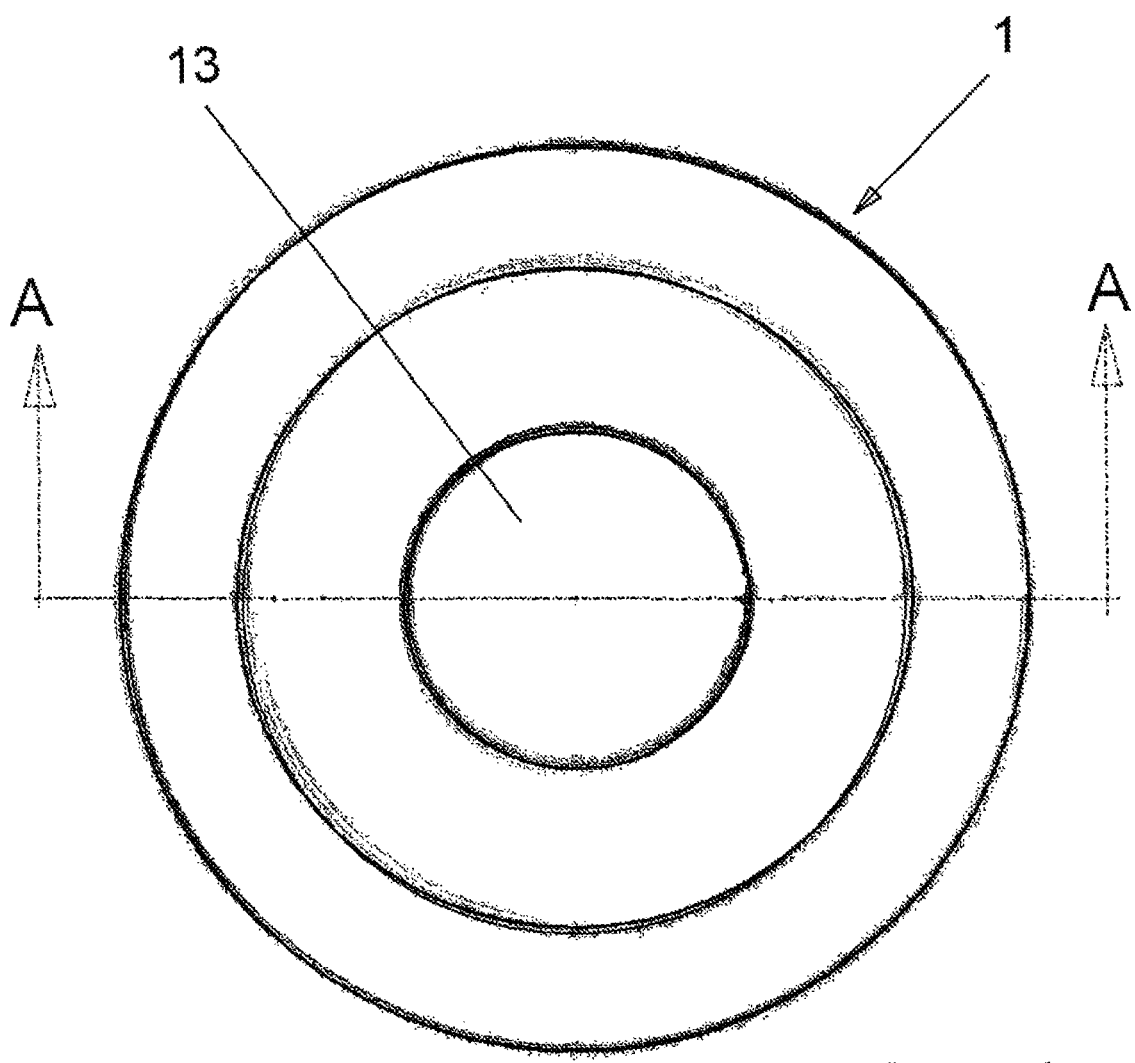
FIG. 1 represents a general plan view of an autonomous neurostimulation unit, according to the invention.
Figure 2:
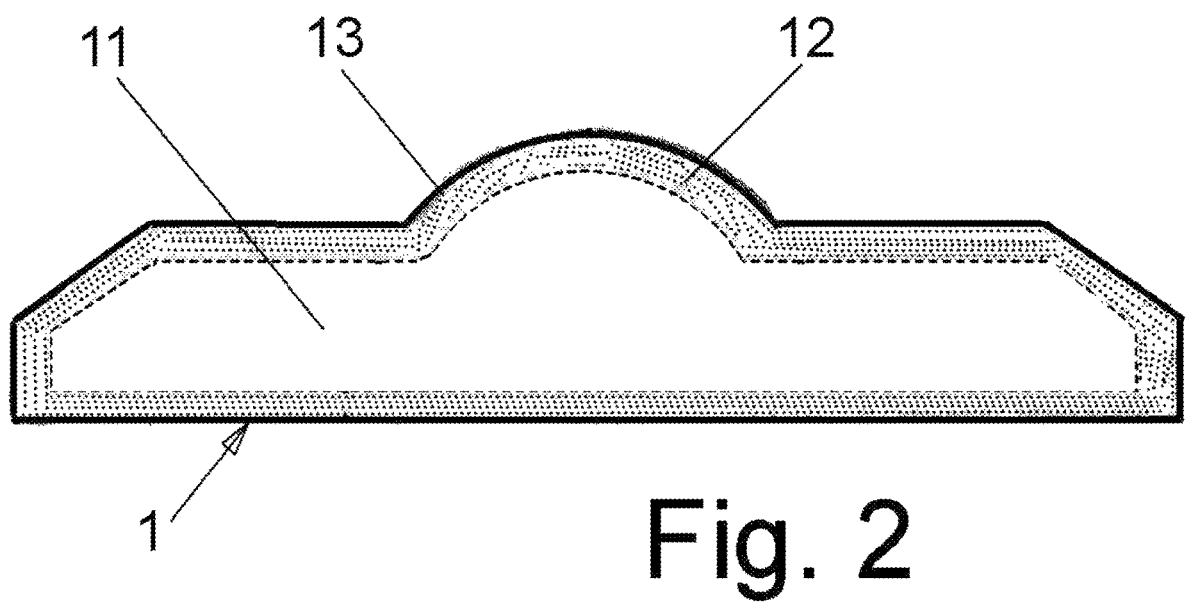
FIG. 2 represents a section in elevated view, according to indication A:A of FIG. 1.

Described below is an example of practical, non-limiting, embodiment of the invention. Other modes of embodiment in which accessory changes are introduced that do not essentially alter it are in no way ruled out.

The object of the invention is an autonomous neurostimulation unit comprised of at least a pair of pads (1) each one of which has:

A ceramic interior (11),

An intermediate layer (12)

A conductive alloy coating (13).

The layers of coating (13) are of different materials in each of the pads (1) that form a pair. Each of the materials has different conductivity. This difference of conductivity helps to create the difference of potentials between the two points in the nervous system channel.

From this basic structuring, any embodiments that do not essentially alter, change or modify the proposal are included in the object of the invention and in particular:

that the intermediate layer (12) uses approximately 1.99% cobalt (% in weight);

that the inner layer (11) uses approximately from 8.33€ to 11.85% phosphorus (% in weight);

that the coating (13) uses approximately, 41.39% gold, 2.32% oxygen and 1.35% cobalt (% in weight);

that the coating (13) uses approximately 98.60% silver (% in weight).

The rest (% in weight being nickel in all cases.

The materials, dimensions, proportions and, in general, those other accessory or secondary details that do not essentially alter, change or modify the proposal can be variable.

The terms in which this report is drafted are a true and accurate reflection of the object described, and must be taken in their broadest sense and never in a limited way.

The invention claimed is:

1. An autonomous neurostimulation unit, used in the modulation of the nervous system comprising at least one pair of pads, each pad comprising at least:
   a) an inner layer of ceramic;
   b) an intermediate layer; and
   c) a conductive alloy coating,
   wherein the autonomous neurostimulation unit does not require external electrical stimulation such that the autonomous neurostimulation unit is configured to modulate electrical information of the nervous system without application of external electrical stimulation, and
   wherein
   a) the inner layer of ceramic comprises about 8-12% wt. of phosphorous;
   b) the intermediate layer comprises about 2% wt. of cobalt; and
   c) the conductive alloy coating comprises about 41% wt. of gold, 2% wt. of oxygen and 1% wt. of cobalt, or about 98% wt. of silver.

2. The autonomous neurostimulation unit according to claim 1, wherein a) the inner layer of ceramic comprises about 8.33% wt. of phosphorous.

3. The autonomous neurostimulation unit according to claim 1, wherein a) the inner layer of ceramic comprises about 11.85% wt. of phosphorous.

4. The autonomous neurostimulation unit according to claim 1, wherein b) the intermediate layer comprises about 1.99% wt of cobalt.

5. The autonomous neurostimulation unit according to claim 1, wherein c) the conductive alloy coating comprises about 41.39% wt. of gold, 2.32% wt. of oxygen and 1.35% wt. of cobalt, or about 98.60% wt. of silver.

* * * * *